United States Patent [19]

Suzuki

[11] 4,172,211
[45] Oct. 23, 1979

[54] PROCESS FOR PREPARING THIOETHERS OF MERCAPTO-ACIDS

[75] Inventor: Shigeto Suzuki, San Francisco, Calif.

[73] Assignee: Chevron Research Company, San Francisco, Calif.

[21] Appl. No.: 892,247

[22] Filed: Mar. 31, 1978

[51] Int. Cl.$^2$ .................. C07C 149/40; C07C 149/26; C07C 149/20

[52] U.S. Cl. ..................... 562/431; 562/426; 562/432; 562/503; 562/507; 562/512; 562/594

[58] Field of Search ............... 260/516, 537 S, 526 S; 562/431, 512, 594, 426, 432, 503, 507

[56] References Cited

U.S. PATENT DOCUMENTS

| | | | |
|---|---|---|---|
| 1,897,516 | 2/1933 | Herz | 260/516 |
| 2,041,705 | 5/1936 | Haddock | 260/516 |
| 2,468,426 | 4/1949 | Cheney | 260/516 |
| 2,884,449 | 4/1959 | Hardy | 260/516 |
| 2,897,081 | 7/1959 | Dersch | 260/516 |
| 3,004,970 | 10/1961 | Skinner | 260/516 |
| 3,355,383 | 11/1967 | Berezin | 260/516 |
| 3,450,771 | 6/1969 | Dombro | 260/516 |
| 3,742,031 | 6/1973 | Lafon | 560/154 |
| 3,743,663 | 7/1973 | Baschany | 260/516 |

FOREIGN PATENT DOCUMENTS 51-56412  5/1976  Japan ................................ 260/526 S

OTHER PUBLICATIONS

Konig, Chem. Ber., 101, pp. 681–693 (1968).
Reid, "Organic Chemistry of Bivalent Sulfur," vol. 2, pp. 16–17, 136, 139, 145, 163 & 189 (1960).
Reid, "Organic Chemistry of Bivalent Sulfur," vol. 3, pp. 181–249 (Chap. 3) (1960).

*Primary Examiner*—James O. Thomas, Jr.
*Assistant Examiner*—Michael Shippen
*Attorney, Agent, or Firm*—D. A. Newell; John Stoner, Jr.; A. T. Bertolli

[57] ABSTRACT

A process for preparing thioethers of mercaptocarboxylic acids by contacting glycolic acid or bromoacetic acid and a mercaptan in the presence of aqueous hydrogen bromide.

9 Claims, No Drawings

PROCESS FOR PREPARING THIOETHERS OF MERCAPTO-ACIDS

BACKGROUND OF THE INVENTION

This invention concerns a process for preparing thioethers of mercapto-carboxylic acids by contacting glycolic acid or bromoacetic acid and a mercaptan in the presence of aqueous hydrogen bromide.

Thioethers of mercapto-carboxylic acids, especially of mercaptoacetic acid, have been prepared and studied previously. The salts and esters of the long-chain alkyl ethers have been found useful as wetting agents, emulsifiers and thickeners for aqueous products. British patent 941,300 describes the use of such compounds as thickeners and the like.

Thioethers of mercaptoacids are generally formed by treating a sodium mercaptide with the sodium salt of a chloroacid, or by addition of an unsaturated compound to the mercaptoacid. E. E. Reid, *Organic Chemistry of Bivalent Sulfur*, Vol. 3, Chemical Publishing Co., Inc., New York, 1960, Chapter 3, thoroughly discusses the preparation and use of thioethers of mercapto-carboxylic acid by such methods. The mercapto acids can be prepared by the reaction of sodium hydrosulfide with sodium chloroacid in an aqueous medium.

SUMMARY OF THE INVENTION

It has now been found that thioethers of mercapto-carboxylic acids can be prepared by contacting glycolic acid or bromoacetic acid with a mercaptan in the presence of aqueous hydrogen bromide. The presence of aqueous hydrogen bromide is critical. If the process is attempted without a catalyst or using another hydrogen halide such as hydrogen chloride, the desired thioether is not produced in significant yields.

DETAILED DESCRIPTION OF THE INVENTION

The over-all reaction to give the thioethers can be described by the reaction formula

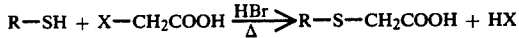

wherein X is either bromide (-Br) or hydroxy (-OH); and wherein R is an alkyl group of 1 to about 20 carbon atoms, an aryl group of 6 to about 12 carbon atoms, a cycloalkyl group of 5 to about 12 carbon atoms, or substituted derivatives of these groups such as carboxyalkyl, carboxyaryl, or carboxycycloalkyl.

The mercaptans which are suitable for use herein may be prepared by several known methods, such as those described in Noller's (Ed.) *Chemistry of Organic Compounds*, 3rd, W. D. Saunders Company, 1966, Chapter 15, pp. 300-304. For purposes of this invention, the mercaptan may contain a variety of organic substituents bound to the sulfur atom. Essentially any substituent which is inert to the condensation of the mercaptan with glycolic acid or bromoacetic acid may be present. For instance, alkyl, aryl, and cycloalkyl mercaptans and their substituted derivatives are suitable. Representative suitable mercaptans include alkyl mercaptans such as methyl, ethyl or propyl mercaptan, and the like; aryl mercaptans such as phenyl mercaptan, benzyl mercaptan, tolyl mercaptans and the like; cycloalkyl mercaptans such as cyclohexyl mercaptan, 3-methyl cyclopentyl mercaptan, 4-chlorocyclooctyl mercaptan, and the like; carboxyalkyl mercaptans such as mercaptoacetic acid, mercaptopropionic acid, and the like; carboxyaryl mercaptans such as 4-mercaptobenzoic acid, and the like; and carboxycycloalkyl mercaptans such as 2-mercaptocyclohexane carboxylic acid, and the like. Preferred mercaptans include the lower alkyl mercaptans such as methyl, ethyl, propyl, and n-octyl mercaptan; and phenyl mercaptan.

Bromoacetic acid and glycolic acid are suitable for use in the process of this invention. Glycolic acid is commercially available or can be prepared by the carbonylation of formaldehyde as described, for instance, by U.S. Pat. No. 3,911,003, granted Oct. 7, 1975, to S. Suzuki. Bromoacetic acid is available from the reaction of glycolic acid and hydrogen bromide.

The process of this invention is carried out in an aqueous medium using conventional batch or continuous equipment over a wide range of temperature and pressure conditions. Suitable temperatures range from about 90° C. to about 220° C., preferably from about 100° C. to about 180° C. Suitable pressures range from about 0.5 atmosphere to about 100 atmospheres; usually the reaction is carried out under autogenous pressure. The process is carried out in the presence of hydrogen bromide. A catalytic amount of hydrogen bromide, that is from about 1 to about 80 weight percent, preferably from about 5 to about 50 weight percent, is required. Thus, a solution of hydrogen bromide gas in water may be used as both the catalyst and the reaction medium. Accordingly, in practice, the concentration of hydrogen bromide ranges from about 1 to about 70 weight percent. The concentration of reactants can also vary greatly. An equimolar amount of the mercaptan and hydroxyacid is acceptable. However, it is preferable to use a molar excess of the mercaptan. Suitable molar ratios of mercaptan to acid range from about 0.5 to about 10, preferably from about 1 to about 5.

In a preferred embodiment, the process is carried out in continuous fashion using an acid-resistant reaction vessel, for instance a Hastelloy alloy or titanium vessel. The reactants are passed into the reactor in contact with aqueous hydrogen bromide. The product stream is withdrawn and unreacted material is recycled. The product can be purified by conventional methods such as distillation or extraction.

EXAMPLES

The following examples further illustrate this invention and are not intended to limit its scope.

EXAMPLE 1

A 300-ml capacity, stainless-steel reactor with a glass liner was charged with glycolic acid 0.1 mol, 48% aqueous HBr 10 ml (containing HBr 0.09 mol and H$_2$O 0.4 mol), and thiophenol 0.15 mol. The reactor was sealed and heated at 150° C. for 2 hours while the reaction mixture was magnetically stirred. The product was extracted with ether, the ether extract was evaporated to dryness, and the residue was methylated in a refluxing methanol with a catalytic amount of sulfuric acid. Analysis of the esterified mixture by gas chromatogram (FFAP column) showed 84% conversion of the glycolic acid with 99% selectivity to thiophenoxyacetic acid.

EXAMPLE 2

The same reactor used in Example 1 was charged with glycolic acid 0.1 mol, 48% aqueous HBr 10 ml (containing HBr 0.09 mol and $H_2O$ 0.4 mol), and ethanethiol 0.30 mol, and the mixture was reacted at 150° C. for 2 hours. The product mixture was evaporated, and the residue was analyzed as before to show 46% conversion of the glycolic acid to ethylthioacetic acid with better than 90% selectivity.

EXAMPLE 3

The same reactor used in Example 1 was charged with glycolic acid 0.1 mol, 48% aqueous HBr 10 ml (containing HBr 0.09 mol and $H_2O$ 0.4 mol), and n-octanethiol 0.15 mol, and the mixture was reacted at 150° C. for 4 hours. The product was evaporated, and the residue was analyzed as before to show 38% conversion of the glycolic acid to n-octylthioacetic acid with 6% selectivity and to thiodiglycolic acid with 90% selectivity.

EXAMPLE 4

The same reactor used in Example 1 was charged with glycolic acid 0.10 mol, aqueous HBr 10 ml (containing HBr 0.09 mol and $H_2O$ 0.4 mol), and mercaptoacetic acid 0.13 mol, and the mixture was reacted at 150° C. for 2 hours. The product mixture was evaporated, and the residue was analyzed as before to show over 99% conversion of glycolic acid to thiodiglycolic acid with better than 95% selectivity.

Replacement of the glycolic acid in the above example with an equal molar amount of bromoacetic acid gave essentially the same result.

What is claimed is:

1. A process for preparing thioethers of mercaptocarboxylic acids which comprises contacting glycolic acid and a mercaptan in the presence of at least of catalytic amount of aqueous hydrogen bromide at a temperature of from about 90° C. to about 220° C. and a pressure of from about 0.5 atmosphere to about 100 atmospheres, said mercaptan having the formula RSH wherein R may be an alkyl group of 1 to about 20 carbon atoms, an aryl group of 6 to about 12 carbon atoms, a cycloalkyl group of 5 to about 12 carbon atoms, or one of the foregoing named groups containing a carboxy substituent.

2. A process according to claim 1 wherein the mercaptan is selected from the group consisting of lower alkyl mercaptans.

3. A process according to claim 2 wherein the mercaptan is selected from the group consisting of methyl, ethyl, propyl, and n-octyl mercaptan.

4. A process according to claim 1 carried out at a temperature from about 100° C. to about 180° C. and autogenous pressure.

5. A process according to claim 1 wherein the mercaptan is an aryl mercaptan.

6. A process according to claim 5 wherein the mercaptan is thiophenol.

7. A process for preparing thioethers of mercaptoacetic acid which comprises contacting a lower alkyl mercaptan and glycolic acid in the presence of aqueous hydrogen bromide at a temperature of from about 100° C. to about 180° C. and autogenous pressure.

8. A process according to claim 7 wherein the mol ratio of mercaptan to glycolic acid is from about 0.5 to about 10.

9. A process according to claim 8 wherein the mercaptan is selected from the group consisting of a lower alkyl mercaptans and the process is carried out at a temperature of from about 100° C. to about 180° C. and autogenous pressure, and the concentration of hydrogen bromide is from about 1 percent to 80 percent by weight.

* * * * *